United States Patent
Estermann et al.

(10) Patent No.: US 9,355,919 B2
(45) Date of Patent: May 31, 2016

(54) METHODS AND SYSTEMS FOR INSPECTING BONDED WAFERS

(75) Inventors: Markus Estermann, Babensham (DE); Christoph Kappel, Aschheim (DE); Reza Kharrazian, Stephanskirchen (DE); Lars Markwort, Haimhausen (DE)

(73) Assignee: Nanda Technologies GmbH, Unterschleissheim (DE)

( * ) Notice: Subject to any disclaimer, the term of this patent is extended or adjusted under 35 U.S.C. 154(b) by 190 days.

(21) Appl. No.: 13/818,967

(22) PCT Filed: Aug. 23, 2011

(86) PCT No.: PCT/EP2011/004229
§ 371 (c)(1),
(2), (4) Date: Feb. 25, 2013

(87) PCT Pub. No.: WO2012/025221
PCT Pub. Date: Mar. 1, 2012

(65) Prior Publication Data
US 2013/0157391 A1 Jun. 20, 2013

(30) Foreign Application Priority Data
Aug. 24, 2010 (EP) .................................. 10008820

(51) Int. Cl.
*H01L 21/66* (2006.01)
*G01N 21/95* (2006.01)

(52) U.S. Cl.
CPC ............ *H01L 22/12* (2013.01); *G01N 21/9501* (2013.01)

(58) Field of Classification Search
None
See application file for complete search history.

(56) References Cited

U.S. PATENT DOCUMENTS

| | | | |
|---|---|---|---|
| 4,883,215 | A | 11/1989 | Goesele et al. |
| 6,086,453 | A | 7/2000 | Fukuoka et al. |

(Continued)

FOREIGN PATENT DOCUMENTS

| | | |
|---|---|---|
| DE | 195 25 770 C1 | 8/1996 |
| DE | 10 2004 058128 A1 | 6/2006 |
| WO | WO 2008/133418 A1 | 11/2008 |
| WO | WO 2009/121628 A2 | 10/2009 |

OTHER PUBLICATIONS

DE19525770, english translation of the IDS reference.*

(Continued)

*Primary Examiner* — Stanetta Isaac
(74) *Attorney, Agent, or Firm* — Silicon Valley Patent Group LLP (57) ABSTRACT

A method of inspecting a bonded wafer 3 arrangement comprises:
directing measuring radiation through the bonded wafer arrangement 3;
imaging at least a portion of the bonded wafer arrangement onto a detector 19 using the measuring radiation having traversed the bonded wafer arrangement, wherein an object side numerical aperture δ of the imaging 16, 18 is less than 0.05; and
simultaneously detecting, using the detector 19, at least a portion of the measuring radiation having traversed the bonded wafer arrangement at a multitude of different spaced apart locations 23 within the field of view;
wherein the detected radiation has an intensity spectrum such that an intensity of the detected radiation having wavelengths less than 700 nm is less than 10% of a total intensity of the detected radiation and an intensity of the detected radiation having wavelengths greater than 1200 nm is less than 10% of the total intensity of the detected radiation.

18 Claims, 5 Drawing Sheets

(56) References Cited

U.S. PATENT DOCUMENTS

2004/0161926 A1    8/2004  Yamaguchi
2005/0073675 A1    4/2005  Lo
2011/0122403 A1*   5/2011  Jang et al. .................. 356/237.1

OTHER PUBLICATIONS

International Search Report mailed on Oct. 24, 2011 for PCT Application No. PCT/EP2011/004229 filed on Aug. 23, 2011, 3 pages.

Machine translation of abstract in English for DE 195 25 770 C1 published on Aug. 29, 1996 visited at www.espacenet.com on Apr. 11, 2013, 1 page.

Machine translation of abstract in English for DE 10 2004 058128 A1 published on Jun. 8, 2006 visited at www.espacenet.com on Apr. 11, 2013, 1 page.

"Optical PTFE The reference for light," Sep. 23, 2015, pp. 1-4, XP055215580, Retrieved from the Internet: URL:http://www.berghof.com/fileadmin/Dateien-Einpflege/Seitenbaum/Home-Downloads/Produkte/PTFE-Produkte/Optisches%20PTFE/Berghof_PTFE-Products_Optical-PTFE.pdf (retrieved on Sep. 23, 2015).

* cited by examiner

A: Particles, scratches and/or residuals on wafer surface
B: Voids, particle inclusions
C: Glue layer defect
D: Glue thickness variation
E: Imaging artefact

METHODS AND SYSTEMS FOR INSPECTING BONDED WAFERS

CROSS-REFERENCE TO RELATED APPLICATIONS

This application is the National Stage of International Patent Application No. PCT/EP2011/004229, filed Aug. 23, 2011, which, in turn, claims the benefit of European Patent Application No. 10 008 820.2, filed Aug. 24, 2010, both of are incorporated herein by reference.

TECHNICAL FIELD

The present disclosure relates to methods and systems for inspecting bonded wafers and methods of semiconductor device manufacture involving bonded wafers.

BACKGROUND

Miniaturized devices are manufactured by applying lithography steps to semiconductor wafers and by bonding wafers or portions of wafers to a carrier substrate, such as a glass substrate or another semiconductor wafer or portion of semiconductor wafer. Some semiconductor manufacturing methods may require thinning of the semiconductor wafer while it is bonded to a carrier substrate. Other manufacturing methods involve bonding patterned wafers to other patterned wafers providing electrical interconnects between the bonded wafers such that three-dimensional semiconductor devices extending across the interface between the wafers are formed.

Wafers can be bonded to substrates by applying an adhesive to the substrate and/or the semiconductor wafer before bringing them into contact which each other and applying an external force. Moreover, direct wafer bonding can be used for bonding two semiconductor wafers together by carrying out an annealing step without any intermediate adhesive.

It is desirable to monitor a quality of a bonded wafer arrangement during its manufacture to improve a yield of manufactured high quality semiconductor devices.

SUMMARY

It is an object of the present disclosure to provide methods and systems for inspecting bonded wafer arrangements and methods of semiconductor device manufacture involving bonded wafer arrangements.

Within the present disclosure, the term bonded wafer arrangement refers to a structure comprising a semiconductor wafer or portion of a semiconductor wafer and a substrate wherein the semiconductor wafer or portion of semiconductor wafer and the substrate are bonded together. An adhesive layer can be provided between the semiconductor wafer and the substrate. The semiconductor wafer may be patterned, i.e. the semiconductor wafer includes a pattern produced in one or more lithography steps, or the semiconductor wafer may be non-patterned, i.e. the semiconductor wafer has not yet undergone lithography steps. The substrate may have the function of a carrier for the semiconductor wafer and include, for example, a glass substrate and a silicon substrate. Moreover, the substrate may be another semiconductor wafer.

According to embodiments, a method of inspecting a bonded wafer arrangement comprises directing measuring radiation onto the bonded wafer arrangement, imaging at least a portion of the bonded wafer arrangement onto a detector using the measuring radiation emerging from the bonded wafer arrangement and simultaneously detecting, using the detector, at least a portion of the measuring radiation emerging from the bonded wafer arrangement at a multitude of different spaced apart locations within the field of view.

The measuring radiation has interacted with the bonded wafer arrangement and carries information relating to the bonded wafer arrangement. Therefore, it is possible to obtain information relating to a quality of the bonded wafer arrangement from an image recorded with the detector.

According to certain embodiments, the bonded wafer arrangement has a front face and a back face, wherein the measuring light is directed onto the front face and wherein the measuring radiation used for the imaging emanates from the front face. Thus, the face of the bonded wafer arrangement onto which the measuring radiation is directed and the face from which the measuring light used for imaging emanates are the same.

According to certain embodiments, the method comprises reflecting measuring radiation having traversed the bonded wafer arrangement and emerging from the back face of the bonded wafer arrangement back through the bonded wafer arrangement. Thus the measuring radiation traverses the bonded wafer arrangement twice.

According to certain other embodiments, the method comprises reflecting measuring radiation having traversed a portion of the bonded wafer arrangement within the bonded wafer arrangement such that it emerges from the front face of the bonded wafer arrangement. For example, patterns provided on the semiconductor wafer which scatter the measuring light can be used to reflect the measuring light within the bonded wafer arrangement.

According to exemplary embodiments herein, the substrate provides the front face onto which the measuring radiation is directed.

According to embodiments, the image recorded with the detector is analyzed to obtain information relating to particles and voids contained between the semiconductor wafer and the substrate and, if an adhesive layer is used, relating to variations of a thickness of the adhesive layer, to deteriorations of the adhesive layer or to other defects that might be present in the bonded wafer arrangement.

According to embodiments, the imaging is performed at a low numerical aperture. According to exemplary embodiments herein, an object side numerical aperture of the imaging is less than 0.1. According to other exemplary embodiments, the object side numerical aperture of the imaging is less than 0.05 or less than 0.03.

The low numerical aperture of the imaging has an effect that an angular spread of arrays of the measuring radiation traversing the bonded wafer arrangement is low. The low angular spread increases a possibility that interferences of the measuring radiation occurring in the bonded wafer arrangement are visible in the image recorded with the detector. Such interferences can be indicative of variations of distances between interfaces formed in the bonded wafer arrangement and of other irregularities and defects included in the bonded wafer arrangement.

According to embodiments, the imaging of the bonded wafer arrangement onto the detector is substantially telecentric at the side of the bonded wafer arrangement. According to exemplary embodiments herein, orientations of chief rays of the detected measuring radiation vary by less than 6° across the portion of the bonded wafer arrangement imaged onto the detector. According to other exemplary embodiments, the orientations of chief rays vary by less than 5° or less than 4°.

The substantially telecentric imaging may have an advantage in that a uniform structure of the bonded wafer arrangement results in a substantial uniform intensity or intensity component within the detected image and that irregularities in the image intensity are indicative of irregularities of the bonded wafer arrangement.

According to embodiments, the field of view covers a significant portion of the bonded wafer arrangement. According to exemplary embodiments herein, the semiconductor wafer of the arrangement has a diameter of 200 mm or more, and the diameter of the field of view is 100 mm or more, such that measuring radiation having traversed the bonded wafer arrangement at locations spaced apart by more than 100 mm can be simultaneously detected with the detector.

According to embodiments, the detected radiation has a limited intensity spectrum substantially from within a wavelength range between 700 nm and 1200 nm. This does not exclude that some amount of radiation having wavelengths outside this rage is detected. However, the substantial amount of radiation has wavelengths from within that wavelength range. According to exemplary embodiments, an intensity of the detected radiation having wavelengths less than 700 nm is less than 10% of a total intensity of the detected radiation, and an intensity of the detected radiation having wavelengths greater than 1200 nm is also less than 10% of the total intensity of the detected radiation.

According to exemplary embodiments, the wavelength range of the detected radiation is even more limited such that an intensity of the detected radiation having wavelengths less than 800 nm is less than 10% of the total intensity of the detected radiation. According to other exemplary embodiments, an intensity of the detected radiation having wavelengths greater than 1100 nm is less than 10% of the total intensity of the detected radiation.

Such limited wavelengths range of the detected radiation has an advantage in that an image contrast of the detected image of the wafer arrangement is high with respect to irregularities or defects of the bonded wafer arrangement.

According to embodiments, a method of semiconductor device manufacture comprises producing a bonded wafer arrangement by bonding a semiconductor wafer to a substrate, and inspecting the bonded wafer arrangement using a method as illustrated above. According to embodiments, the method of manufacture includes a decision as to whether further manufacturing steps are applied to the bonded wafer arrangement or not. Such decision includes determining predefined criteria based on the inspection, wherein the further manufacturing steps are applied to the bonded wafer system only if the predefined criteria are fulfilled.

The predefined criteria can be selected such that they are indicative of a quality of the bonded wafer arrangement and such that the predefined criteria are not fulfilled if the bonded wafer arrangement includes defects.

According to exemplary embodiments herein, a de-bonding is applied to the bonded wafer arrangement to separate the semiconductor wafer from the substrate if the predefined criteria are not fulfilled. The semiconductor wafer can then be used to produce a new bonded wafer arrangement which can be inspected again. It is thus possible to avoid additional manufacturing steps applied to a defective bonded wafer arrangement.

According to exemplary embodiments, the semiconductor wafer of the bonded wafer arrangement is thinned. According to exemplary embodiments herein, an initially thick semiconductor wafer having a thickness of, for example, more than 500 μm is thinned to have a thickness of, for example, less than 100 μm or less than 50 μm.

According to embodiments, the inspecting includes identifying defect locations of the bonded wafer arrangement, dicing the bonded wafer arrangement to form a plurality of semiconductor elements, and further processing only those semiconductor elements not containing at least one identified defect location.

It is thus possible to avoid unnecessary processing of semiconductor elements including one or more defect locations.

According to embodiments, a bonded wafer inspection system which can be used in a bonded wafer inspection method comprises a camera and imaging optics imaging a field of view onto the camera, a reflector having a diffuse reflection characteristics, a bonded wafer loading apparatus configured to position a bonded wafer arrangement at a measurement position within the field of view such that the bonded wafer arrangement is located between the reflector and the imaging optics, and illumination optics configured to direct an illumination beam of radiation onto the reflector such that it traverses the bonded wafer arrangement.

Radiation reflected from the reflector traverses the bonded wafer arrangement and is received by the camera. The bonded wafer arrangement is imaged onto the camera, and light intensity changes and interferencies caused by the bonded wafer arrangement generate an image contrast in the image detected by the camera.

The diffuse reflection characteristics of the reflector has an advantage in that measuring radiation from a broad angular range traverses the bonded wafer arrangement such that measuring radiation having traversed the bonded wafer arrangement is supplied at a substantially uniform intensity to a substantially complete angular range of measuring radiation accepted by the imaging optics and supplied to the camera.

According to embodiments, the imaging optics is configured such that an object side numerical aperture is less than 0.05 and/or such that orientations of imaging chief rays vary by less than 6° across the imaged portion of the bonded wafer arrangement. The small numerical aperture has an advantage in producing a considerable image contrast resulting from deteriorations and defects of the bonded wafer arrangement while the diffuse reflection characteristics of the reflector ensures that measuring radiation is available for the full angular range of radiation accepted by the imaging optics and supplied to the detector.

According to further exemplary embodiments, at least one spectral filter is provided in a beam path extending from a light source of the illumination optics via the reflector to a radiation sensitive substrate of the camera, wherein the at least one spectral filter is configured such that it blocks light having wavelengths less than 700 nm and/or such that it blocks light having wavelengths greater than 1200 nm.

BRIEF DESCRIPTION OF THE DRAWINGS

The foregoing as well as other advantageous features of the present disclosure will be more apparent from the following detailed description of exemplary embodiments with reference to the accompanying drawings. It is noticed that all possible embodiments of the present invention necessarily exhibit each and every, or any, of the advantages identified herein.

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the above summary should be referred to.

Figure 1:
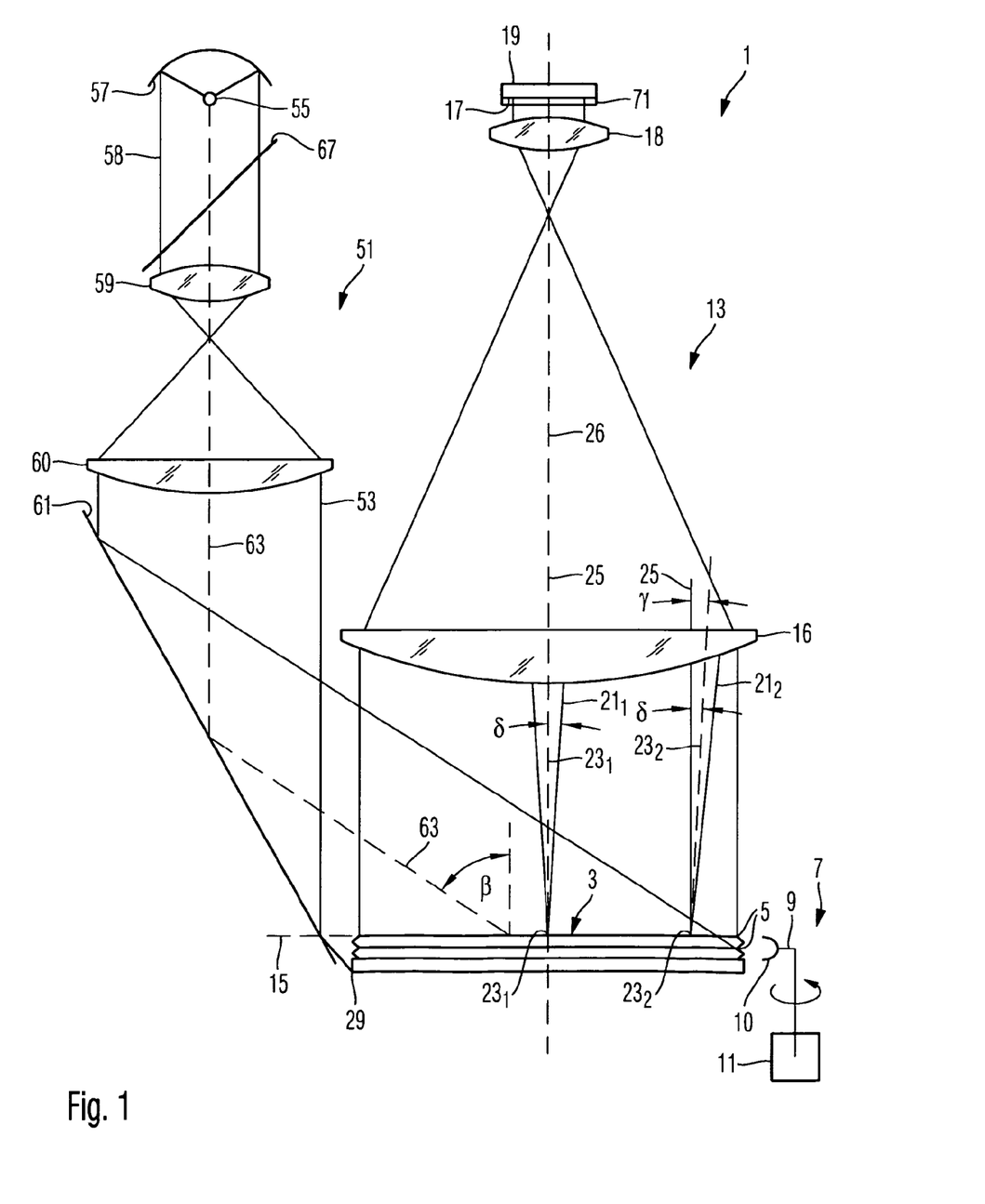
FIG. 1 is a schematic illustration of an embodiment of a bonded wafer inspection system.

FIG. 1 is a schematic illustration of a system 1 which is configured to inspect a bonded wafer arrangement 3. In the illustrated example, the bonded wafer arrangement 3 comprises two semiconductor wafers 5 which are bonded together by an adhesive provided between the opposite surfaces of the two semiconductor wafers 5. According to other examples, the bonded wafer arrangement comprises more than two semiconductor wafers attached to each other, or only one semiconductor wafer which is attached to a carrier substrate which can be made of glass, for example. The one or more semiconductor wafers of the bonded wafer arrangement may have various thicknesses. For example, a thickness of such semiconductor wafer can be in a range from 200 µm to 750 µm. According to other examples, one or more semiconductor wafers of the bonded wafer arrangement are thinned wafers having a thickness of less than 100 µm or less than 50 µm, for example.

The inspection system 1 comprises a bonded wafer loading apparatus 7 configured to position the bonded wafer arrangement 5 at and to remove the bonded wafer arrangement 5 from a measurement position of the inspection system 1. In the illustration of FIG. 1, the bonded wafer arrangement 3 is positioned at the measurement position of the inspection system, and the loading apparatus 7 may comprise an arm 9, a gripper 10 or similar tool configured to attach the bonded wafer arrangement 3 to the arm 9, and an actuator 11 configured to move the bonded wafer arrangement 3 attached to the arm 9 away from the measurement position shown in FIG. 1 or into the measurement position.

The semiconductor wafers of the bonded wafer arrangement may have an arbitrary diameter. Typical diameters are about 200 mm and about 300 mm, wherein bonded wafer arrangements of even greater diameters can be inspected using the system 1.

When the bonded wafer arrangement 3 is positioned at the measurement position of the inspection system 1, the bonded wafer arrangement 3 is located within a field of view of an imaging optics 13 of the inspection system 1. The imaging optics 13 comprises plural lenses to image an object plane 15 onto a radiation sensitive surface 17 of a camera 19. In the schematic illustration of FIG. 1, the imaging optics 13 has two lenses 16 and 18. In practice, the imaging optics 13 will have a higher number of lenses such that the imaging optics 13 fulfil certain requirements with respect to imaging quality. An example of suitable imaging optics which can be used in the illustrated embodiment of the bonded wafer inspection system 1 is disclosed in WO 2009/121628 A1, the full disclosure of which is incorporated herein by reference.

In the present example, the field of view of the imaging optics has a lateral extension such that the whole bonded wafer arrangement 3 fits within the field of view such that the inspection system 1 is a full wafer inspection system. According to other examples, the bonded wafer arrangement does not fit completely within the field of view of the imaging optics. However, a substantial amount, such as more than 10% or more than 20% of the total surface area of the bonded wafer arrangement are covered by the field of view of the imaging optics. It is then for example possible to obtain an image of the full bonded wafer arrangement by stitching together a sufficiently low number of ten or less individual images obtained from different portions of the bonded wafer arrangement. In both examples, the inspection system 1 can be referred to as a macro inspection system since a limited spatial resolution of the detector 19 and the large extension of the field of view prevent direct detection of individual micro defects contained in the bonded wafer arrangement 13. For example, a portion of the bonded wafer arrangement having a surface area of 100 µm·100 µm is imaged onto one pixel of the detector 19. It is apparent that, in general, only macro defects having lateral extensions greater than 0.01 $mm^2$ can be directly detected with the bonded wafer inspection system 1. Moreover, the imaging optics 13 has a low object side numerical aperture. The numerical aperture (NA) of the imaging optics 13 is a dimensionless number that characterizes the range of angles over which the system can accept light for imaging the object plane 15 onto the light sensitive surface 17 of the detector 19. The range of angles accepted by the system 13 for imaging is indicated in FIG. 1 by exemplary cones $21_1$ and $21_2$ of rays of radiation originating from exemplary spaced apart locations $23_1$ and $23_2$ on the object plane 15. The cones $21_1$ and $21_2$ have a half opening angle δ, and the sine of the half opening angle δ is commonly referred to as the numerical aperture NA on the object side of the imaging optics 13. Exemplary values of numerical apertures of the imaging system 13 are 0.05, 0.025 or 0.015.

Apart from the relatively low numerical aperture, the imaging optics 13 does also have a telecentric property which is also illustrated in FIG. 1. Chief rays $23_1$ and $23_2$ are oriented under angles δ relative to surface normals 25 of the object plane 15. The imaging optics 13 is configured such that the angles δ, i.e. the orientations of the chief rays 23, vary by less than 6° across the field of view of the imaging optics 13.

The bonded wafer arrangement 3 positioned at the measurement position is located between a reflector 29 and the lens 16 of the imaging optics 13 close to the object plane 15. In the illustrated example, the reflector 29 is a ceramics substrate having an upper surface oriented towards the lens 16 of the imaging optics 13 close to the object plane, wherein the substrate of the reflector 29 is oriented parallel to the substrate and semiconductor wafer 5 of the bonded wafer arrangement 3. Moreover, the substrate of the reflector 29 is positioned close to the bonded wafer arrangement 3. According to other examples, the reflector 29 is positioned at a distance from the bonded wafer arrangement 3 and oriented under an angle relative to the bonded wafer arrangement 3. For example, an angle between a surface normal of the reflector 29 and a surface normal of the semiconductor wafer of the bonded wafer arrangement 3 can be up to 20°.

In the illustrated example, the substrate of the reflector 29 has a flat surface. According to other examples, the surface of the reflector may have a curved shape, however.

Figure 2:
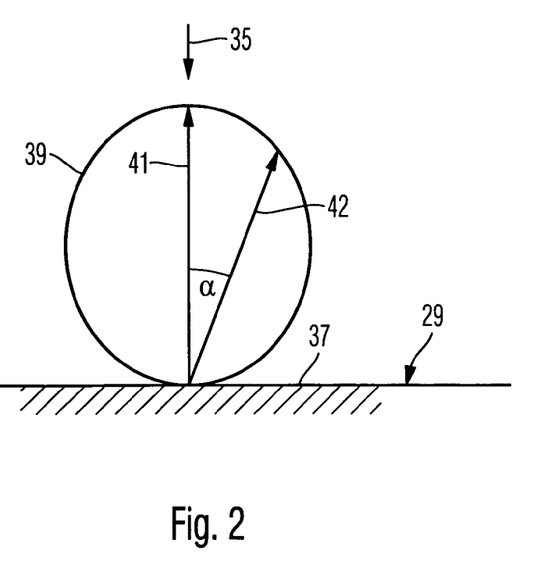
FIG. 2 is an illustration of a reflection characteristics of a reflector used in the bonded wafer inspection system shown in FIG. 1.

The reflector 29 has a diffuse reflection characteristics illustrated in FIG. 2. FIG. 2 shows a situation where a collimated beam 35 of radiation is orthogonally incident on a surface 37 of the reflector 29. An envelope line 39 represents an angular distribution of intensities of light of the incident beam 35 reflected from the surface 37. An arrow 41 indicates a maximum intensity of the reflected radiation and is oriented orthogonal to the surface 37. An arrow 42 illustrates an intensity of radiation reflected from the surface 37 in a direction oriented under an angle α relative to the surface normal. The intensity 42 is smaller than the maximum intensity 41. However, the intensity 42 is considerably greater than it would be the case if the reflector 29 was a specular reflector. The reflector 29 is a diffuse reflector such that, for example, the intensity 42 of radiation reflected in a direction oriented under 20° relative to the surface normal has an intensity of more than 0.5 times the maximum intensity or more. If the reflector 29 was an ideal diffuse reflector, the reflection characteristics would follow Lambert's law, and the intensity in the direction oriented under 20° relative to the surface normal would be about 0.94 times the maximum intensity. In practice, the reflection characteristics of the diffuse reflector 29 will deviate from Lambert's law. According to examples, the reflector 29 can be made of a ceramics material.

The bonded wafer inspection system 1 comprises illuminating optics 51 configured to illuminate the reflector 29 with a beam of measuring radiation. For this purpose, the illumination optics 51 comprises a radiation source 55 to emit the measuring radiation, a mirror 57 or other optical elements to collimate the emitted measuring radiation to form a beam 58, and a plurality of lenses 59, 60 to produce the beam 53 such that the beam has a desired cross section and intensity profile. The illumination optics 21 further comprises a mirror 61 to reflect the beam 53 such that it is incident on the reflector 29 through the bonded wafer arrangement 3 when it is positioned in the measurement position of the imaging optics 13.

In the schematic illustration of FIG. 1, the illumination optics 51 has two lenses 59 and 60. In practical embodiments, the illumination optics 51 will have a more complicated configuration. An example of suitable illumination optics is disclosed in WO 2009/121628 A1, the disclosure of which is incorporated herein by reference.

An optical axis 63 of the illumination optics 51 intersects the object plane 15 of the imaging optics 13 such that an angle between the axis 63 and an optical axis 26 of the imaging optics 13 is greater than 20° or greater than 30° but smaller than 85° or smaller than 80°.

The radiation source 55 can be a xenon arc lamp, for example. The radiation source 55 produces a broad spectrum of radiation, including visible light and infrared radiation. A mirror 67 is positioned in the beam path of the illumination optics 51, wherein the mirror is configured such that it reflects visible light and allows infrared radiation to pass through, such that the mirror 67 has a function of a visible light filter. According to other examples, the mirror can be configured such that it allows visible light to pass through and reflects infrared light, wherein the reflected light is used to provide the beam 53 of illumination radiation.

The radiation of the illumination beam traverses the bonded wafer arrangement 3 and is incident on the reflector 29. The radiation having traversed the bonded wafer arrangement 3 is reflected at the reflector 29 according to the diffuse reflection characteristics such that a substantial amount of reflected illumination radiation is available to traverse the bonded wafer arrangement 3 again and such that it is accepted by the imaging optics 13 and supplied to the detector 19. Images recorded by the detector 19 from measuring light having traversed the bonded wafer arrangement 3 include information relating to a quality of the bonded wafer arrangement as will be further illustrated below.

The imaging optics 13 includes a filter 71 positioned in front of the radiation sensitive surface 17 of the camera 19, wherein the filter 71 blocks far infrared radiation.

In the example illustrated in FIG. 1, a filter (mirror 67) blocking visible light is positioned in the illumination beam path, and a filter (filter 71) blocking far infrared light is positioned in the imaging beam path. According to other examples, the filter blocking the visible light is positioned in the imaging beam path and the filter blocking the far infrared light is positioned in the illumination beam path, and according to still other examples, both filters are positioned in one of the illumination beam path and the imaging beam path. According to still further examples, the two filters are incorporated in one single filter element providing a band path characteristics for infrared radiation.

According to some examples, the filter blocking the visible light blocks light having wavelengths below 700 nm or below 800 nm. According to further examples, the filter blocking the far infrared radiation blocks radiation having wavelengths greater than 1200 nm or greater than 1250 nm.

Figure 3:
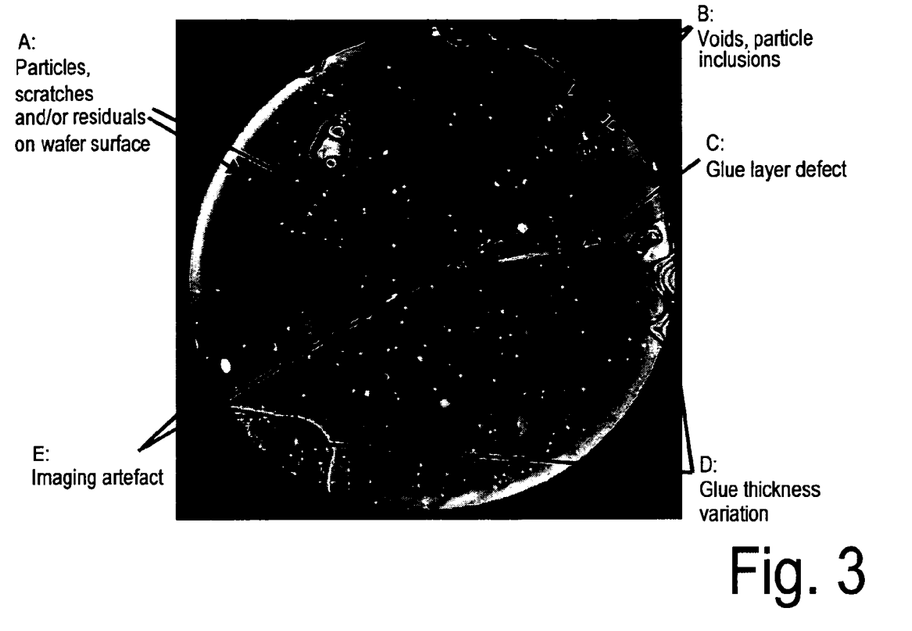
FIG. 3 shows an exemplary image of a bonded wafer arrangement recorded with the bonded wafer inspection system shown in FIG. 1.

FIG. 3 shows an image obtained by inspecting a bonded wafer arrangement using the inspection system shown in FIG. 1. The imaged bonded waver arrangement consists of two semiconductor wafers each having a diameter of 300 mm and a thickness of about 750 nm bonded together with an adhesive layer having a thickness of about 15 μm. While the wafers of the bonded wafer arrangement of the imaged example are unpatterned wafers having a substantially uniform structure, the image of the bonded wafer arrangement contains a surprising amount of information at a high image contrast: For example, image features indicated at A have been identified to correspond to defects such as particles, scratches and residuals on the surfaces of the semiconductor wafers. Image features indicated at B have been found to correspond to voids and particle inclusions between the two bonded wafers. Image features indicated at C have been found to correspond to defects in the bonding adhesive layer. Image features indicated at D have been found to correspond to variations in a thickness of the adhesive layer provided between the bonded wafers. Finally, it has not yet been possible to find a correspondence between image features indicated at E in FIG. 3 and structures or defects of the bonded wafer arrangement, such that these features indicated at E seem to represent imaging artefacts.

Figure 4:
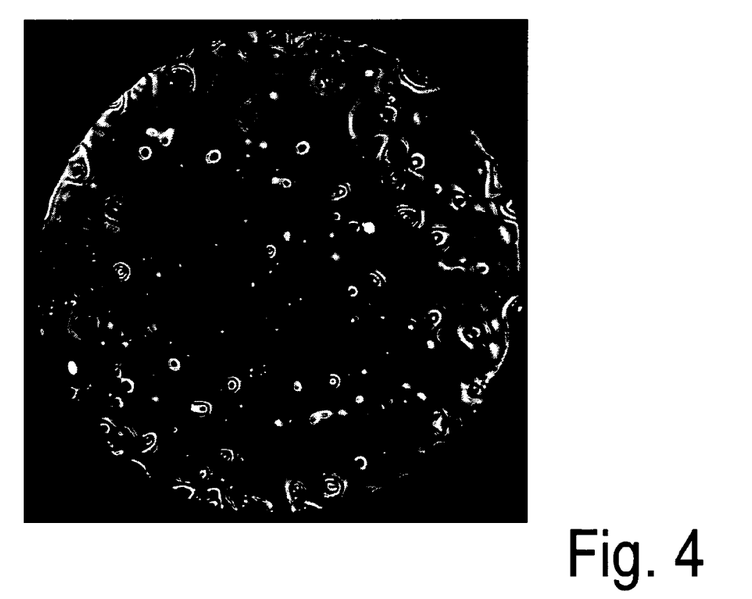
FIG. 4 shows a further exemplary image of a bonded wafer arrangement recorded with the bonded wafer inspection system shown in FIG. 1.

FIG. 4 shows an image obtained from a bonded wafer arrangement using the inspection system illustrated with reference to FIG. 1 above, wherein the bonded wafer arrangement comprises two semiconductor wafers having a diameter of 300 mm bonded to each other using an adhesive layer of a thickness of 15 μm, for example. A thickness of one semiconductor wafer of the imaged arrangement is about 750 μm while the other wafer is a thinned wafer having a thickness of, for example, 30 μm. The image has a rich structure at a high image contrast wherein these structures appear to relate to voids and particle inclusions and thickness variations of the adhesive layer.

From FIGS. 3 and 4 it is apparent that the imaging of the bonded wafer arrangement provides valuable information relating to a quality of the bonded wafer arrangement. This information can be extracted from the image and used to control the manufacture of semiconductor devices involving the bonded wafer arrangement.

Figure 5:
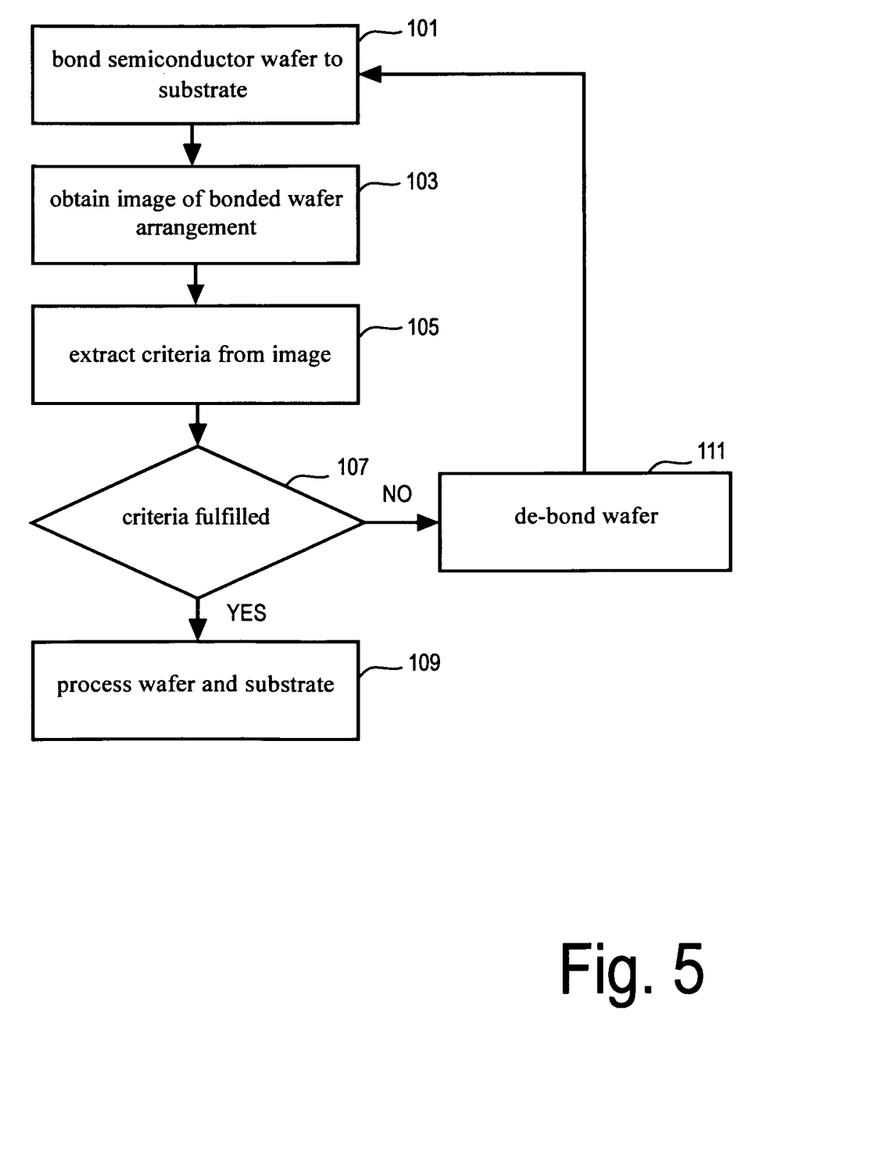
FIG. 5 is a flow chart of an embodiment of a semiconductor device manufacture method and FIG. 6 is a flow chart of a further embodiment of a semiconductor device manufacture method.

FIG. 5 is a flow chart of an embodiment of a method of semiconductor device manufacture. The method comprises producing a bonded wafer arrangement in a step 101 by bonding a semiconductor wafer to a substrate. An image of the bonded wafer arrangement is obtained using a bonded wafer inspection system, such as the system illustrated with reference to FIG. 1 above, in a step 103. The image is analyzed in a step 105 and predefined criteria are extracted from the image. The criteria may comprise an amount of particles, scratches, residuals, de-laminations and voids, adhesive layer defects, i.e. crystallization in the adhesive layer and thickness variations of the adhesive layer found in the image. In a step 107 it is decided whether the imaged bonded wafer arrangement fulfils the predefined criteria. For example, the criteria may include predefined thresholds for the above mentioned amounts. If the criteria are fulfilled, for example, because the amounts are below the predefined thresholds, processing is continued at a step 109 in which the bonded wafer arrangement is further processed by required processing steps including, for example, thinning of the semiconductor wafer and etching steps as necessary in the manufacture of semiconductor devices involving the bonded wafer arrangement. If the predefined criteria are not fulfilled in the decision step 107, which means that a yield of high quality semiconductor devices would decline if the imaged bonded wafer arrangement was further processed in step 109, the bonded wafer arrangement is de-bonded in a step 111. It is then possible to process the semiconductor wafer and the substrate separately by steps such as de-bonding and cleaning, and to use the recovered semiconductor wafer and substrate in a new step of producing the bonded wafer arrangement.

Figure 6:
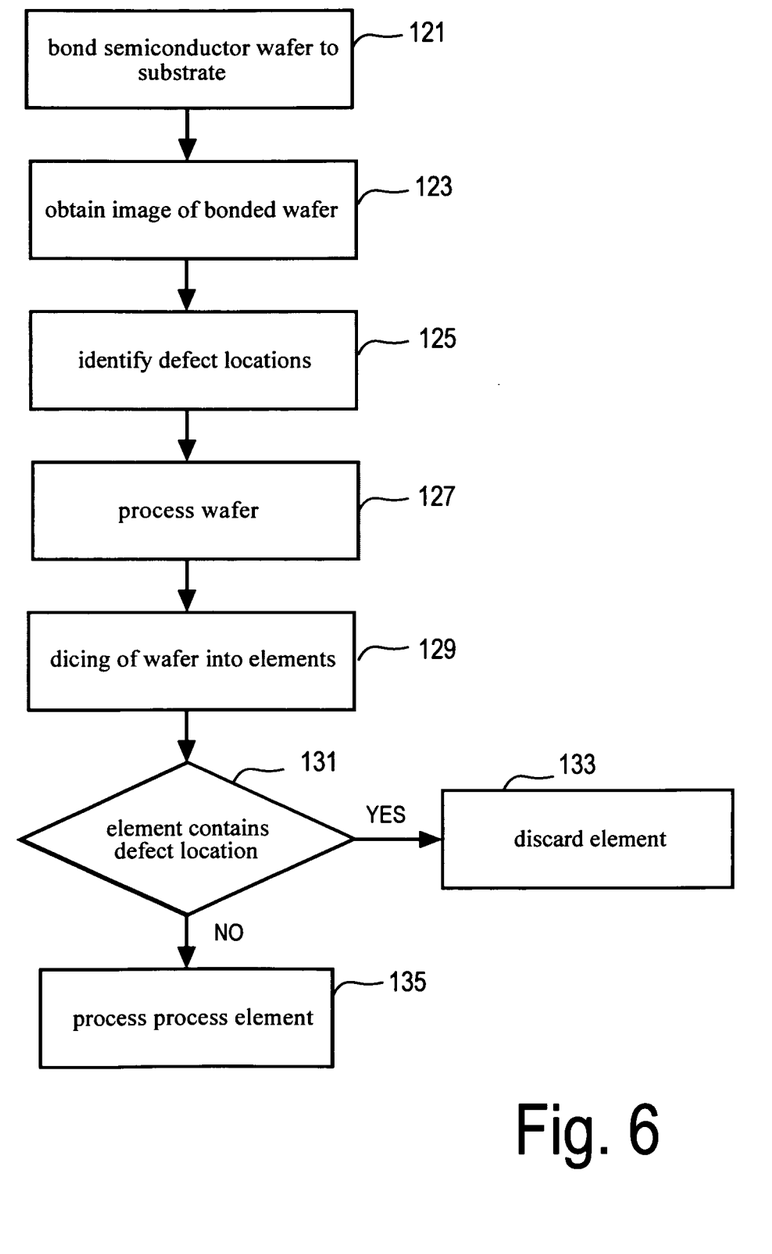

FIG. 6 shows a flow chart of a further embodiment of a method of semiconductor device manufacture. The method comprises a step 121 of producing a bonded wafer arrangement, a step 123 of imaging the bonded wafer arrangement and a step 125 of analyzing the image of the bonded wafer arrangement. This analysis includes identifying locations on the bonded wafer arrangement at which defects are found. For examples, those locations of the bonded wafer arrangement can be identified as defect locations which correspond to locations in the image where a particle, scratch, residuals, de-lamination and void, particle inclusion, defect of the adhesive layer, i.e. crystallization in the adhesive layer and thickness variation of the adhesive layer, is found. The identified defect locations are memorized in step 125. Subsequent to the imaging of the bonded wafer arrangement in step 123, the arrangement undergoes further processing, such as thinning and etching, in a step 127. When the processing of the bonded wafer arrangement is completed, it will be separated in two elements in a dicing step 129, wherein semiconductor devices will be manufactured from the separated elements.

A decision 131 is made for every separated element as to whether it should be further processed or not. This decision is based on the position or area which the separated element occupied in the bonded wafer arrangement before dicing. If this occupied area contains a location identified as a defect location in step 125, the element will be discarded in a step 133 to avoid unnecessary subsequent manufacturing steps applied to this element which would probably result in a defective semiconductor device. Only those elements originating from positions in the bonded wafer arrangement not containing defect locations identified in step 125 will be further processed in a step 135 in which the manufacture of the semiconductor device is continued.

In the embodiments illustrated with reference to FIG. 1, a reflector is provided below the bonded wafer arrangement in order to reflect back the measuring radiation such that the measuring radiation used for the imaging has traversed the complete bonded wafer arrangement twice. According to other embodiments, such separate reflector is not necessary. In these embodiments, at least one wafer of the bonded wafer arrangement is a patterned wafer including patterns which may scatter measuring radiation. The patterns are provided within the patterned wafer arrangement, such that measuring radiation having traversed a thickness portion of the wafer arrangement is reflected at the patterns such that it finally emerges from the front face of the arrangement.

While the invention has been described with respect to certain exemplary embodiments, it is evident that any alternatives, modifications and variations will be apparent to those skilled in the art. Accordingly, the exemplary embodiments set forth herein are intended to be illustrative and not limiting in any way. Various changes may be made without departing from the spirit and scope of the present invention as defined in the following claims.

The invention claimed is:

1. A method of inspecting a bonded wafer arrangement, wherein the bonded wafer arrangement includes plural layers of a semiconductor wafer and at least one of an adhesive layer and a substrate attached to the semiconductor wafer, and wherein the method comprises:
directing measuring radiation onto the bonded wafer arrangement;
imaging at least a portion of the bonded wafer arrangement onto a detector using the measuring radiation having emerging from the bonded wafer arrangement, wherein an object side numerical aperture of the imaging is less than 0.05, wherein the bonded wafer arrangement has a front face and a back face, wherein the measuring radiation is directed onto the front face and wherein the measuring radiation used for the imaging emanates from the front face; and
simultaneously detecting, using the detector, at least a portion of the measuring radiation emerging from the bonded wafer arrangement at a multitude of different spaced apart locations within the field of view;
wherein the detected radiation has an intensity spectrum such that an intensity of the detected radiation having wavelengths less than 700 nm is less than 10% of a total intensity of the detected radiation and an intensity of the detected radiation having wavelengths greater than 1200 nm is less than 10% of the total intensity of the detected radiation.

2. The method according to claim 1, wherein the simultaneously detecting comprises detecting the measuring radiation having traversed the bonded wafer arrangement at locations spaced apart by more than 100 mm.

3. The method according to claim 1, wherein orientations of chief rays of the detected radiation used for imaging vary by less than 6° across the portion of the bonded wafer arrangement imaged onto the detector.

4. The method according to claim 1, further comprising reflecting measuring radiation having traversed the bonded wafer arrangement and emerging from the back face of the bonded wafer arrangement back through the bonded wafer arrangement.

5. The method according to claim 1, further comprising reflecting measuring radiation having traversed a portion of the bonded wafer arrangement within the bonded wafer arrangement such that it emerges from the front face of the bonded wafer arrangement.

6. The method according to claim 5, wherein the measuring radiation is reflected at patterns provided on the semiconductor wafer.

7. The method according to claim 5, wherein the substrate provides the front face.

8. The method according to claim 1, further comprising analyzing the detected measuring radiation and determining at least one of variations of a thickness of the adhesive layer, de-lamination and voids between the semiconductor wafer and the substrate, particles and areas of adhesive layer inhomogeneities due to crystallization formed between the semiconductor wafer and the substrate.

9. A method of semiconductor device manufacture, comprising:
producing a bonded wafer arrangement by bonding a semiconductor wafer to a substrate; and
inspecting the bonded wafer arrangement comprising:
wherein the bonded wafer arrangement includes plural layers of a semiconductor wafer and at least one of an adhesive layer and a substrate attached to the semiconductor wafer, and wherein the method comprises:
directing measuring radiation onto the bonded wafer arrangement;
imaging at least a portion of the bonded wafer arrangement onto a detector using the measuring radiation having emerging from the bonded wafer arrangement, wherein an object side numerical aperture of the imaging is less than 0.05, wherein the bonded wafer arrangement has a front face and a back face, wherein the measuring radiation is directed onto the front face and wherein the measuring radiation used for the imaging emanates from the front face; and
simultaneously detecting, using the detector, at least a portion of the measuring radiation emerging from the bonded wafer arrangement at a multitude of different spaced apart locations within the field of view;
wherein the detected radiation has an intensity spectrum such that an intensity of the detected radiation having wavelengths less than 700 nm is less than 10% of a total intensity of the detected radiation and an intensity of the detected radiation having wavelengths greater than 1200 nm is less than 10% of the total intensity of the detected radiation.

10. The method according to claim 9, further comprising thinning of the semiconductor wafer if a result of the inspecting fulfills predefined criteria, and de-bonding the semiconductor wafer from the substrate if the result of the inspecting does not fulfill the predefined criteria.

11. The method according to claim 9, further comprising:
identifying defect locations of the bonded wafer arrangement;
dicing the bonded wafer arrangement into a plurality of semiconductor elements; and
processing the semiconductor elements formed of portions of the bonded wafer arrangement not containing at least one identified defect location while not processing the semiconductor elements formed of portions of the bonded wafer arrangement containing at least one identified defect location.

12. A bonded wafer inspection system comprising:
a camera and imaging optics imaging a field of view onto the camera;
a reflector having a diffuse reflection characteristics;
a bonded wafer loading apparatus configured to position a bonded wafer arrangement at a measurement position within the field of view such that the bonded wafer arrangement is located between the reflector and the imaging optics; and
illumination optics configured to direct an illumination beam of radiation through the bonded wafer arrangement onto the reflector, wherein the illumination beam is reflected off the reflector, passes through the bonded wafer arrangement a second time and is received by the imaging optics.

13. The bonded wafer inspection system according to claim 12, wherein an optical axis of the imaging optics is oriented under an angle greater than 30° relative to an optical axis of the illumination optics.

14. The bonded wafer inspection system according to claim 12, wherein a surface size of the reflector is at least 90% of an area size of the bonded wafer arrangement positioned within the field of view.

15. The bonded wafer inspection system according to one claim 12, wherein a surface normal of the reflector is oriented under an angle of less than 20° relative to an optical axis of the imaging optics.

16. The bonded wafer inspection system according to claim 12, wherein the reflector has the diffuse reflecting characteristics such that, when a collimated beam of radiation is orthogonally incident on a surface of the reflector and an intensity of light reflected from the surface into a direction orthogonal to the surface of the reflector is a maximum intensity, an intensity of light reflected in a direction oriented under an angle of 20° relative to the orthogonal direction has an intensity greater than 0.5 times the maximum intensity.

17. The bonded wafer inspection system according to claim 12, wherein the imaging optics is configured such that a numerical aperture at the measurement position is less than 0.05 and/or such that orientations of imaging chief rays vary by less than 6° across the portion of the bonded wafer arrangement imaged onto the detector.

18. The bonded wafer inspection system according to claim 12, wherein at least one spectral filter is provided in a beam path extending from a light source of the illumination optics via the reflector to an image sensor of the camera, wherein the at least one spectral filter is configured such that it blocks light having wavelengths less than 700 nm and/or such that it blocks light having wavelengths greater than 1200 nm.

* * * * *